(12) United States Patent
Marino et al.

(10) Patent No.: US 6,387,070 B1
(45) Date of Patent: May 14, 2002

(54) BONE SLURRY RECOVERY

(75) Inventors: James F. Marino, La Jolla; Nicolei R. King, San Diego, both of CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/663,049

(22) Filed: Sep. 15, 2000

Related U.S. Application Data

(60) Provisional application No. 60/154,449, filed on Sep. 17, 1999.

(51) Int. Cl.$^7$ .............................................. A61M 1/00
(52) U.S. Cl. .......................... 604/35; 210/256; 494/36; 433/92
(58) Field of Search .......................... 604/35, 36, 4.01, 604/5.01, 5.04, 6.09, 27, 28, 540, 317, 319; 494/36, 37, 60; 606/170; D24/219; 210/255, 256, 321.6, 433.1, 532.1, 304, 512.1, 781, 521, 578, 540, 532.2, 800, 305, 301; 433/92

(56) References Cited

U.S. PATENT DOCUMENTS

| 148,513 A | 3/1874 | Senderling |
| 745,870 A | * 12/1903 | Lowe .......................... 210/305 |
| 1,179,327 A | * 4/1916 | Kearney ...................... 210/305 |
| 1,738,521 A | * 12/1929 | Bomhoff ...................... 210/301 |
| 2,846,073 A | 8/1958 | Hopper |
| 4,385,891 A | * 5/1983 | Ligotti ......................... 433/92 |
| 4,445,509 A | 5/1984 | Auth |
| 4,533,471 A | 8/1985 | Collins, Jr. |
| 5,354,468 A | * 10/1994 | Richards ...................... 433/92 |
| 5,472,605 A | 12/1995 | Zuk, Jr. |
| 5,489,291 A | 2/1996 | Wiley |

FOREIGN PATENT DOCUMENTS

EP 0069449 1/1983

* cited by examiner

Primary Examiner—David O. Reip
Assistant Examiner—Julian W. Woo
(74) Attorney, Agent, or Firm—Jonathan Spangler

(57) ABSTRACT

A system for recovering bone particles removed from a patient, comprising a sub-system for removing particles of bone; a sub-system for irrigating the operative site to yield a slurry comprising the bone particles; a sub-system for removing the slurry from the operative site; and a sub-system for recovering the bone particles from the slurry.

7 Claims, 8 Drawing Sheets

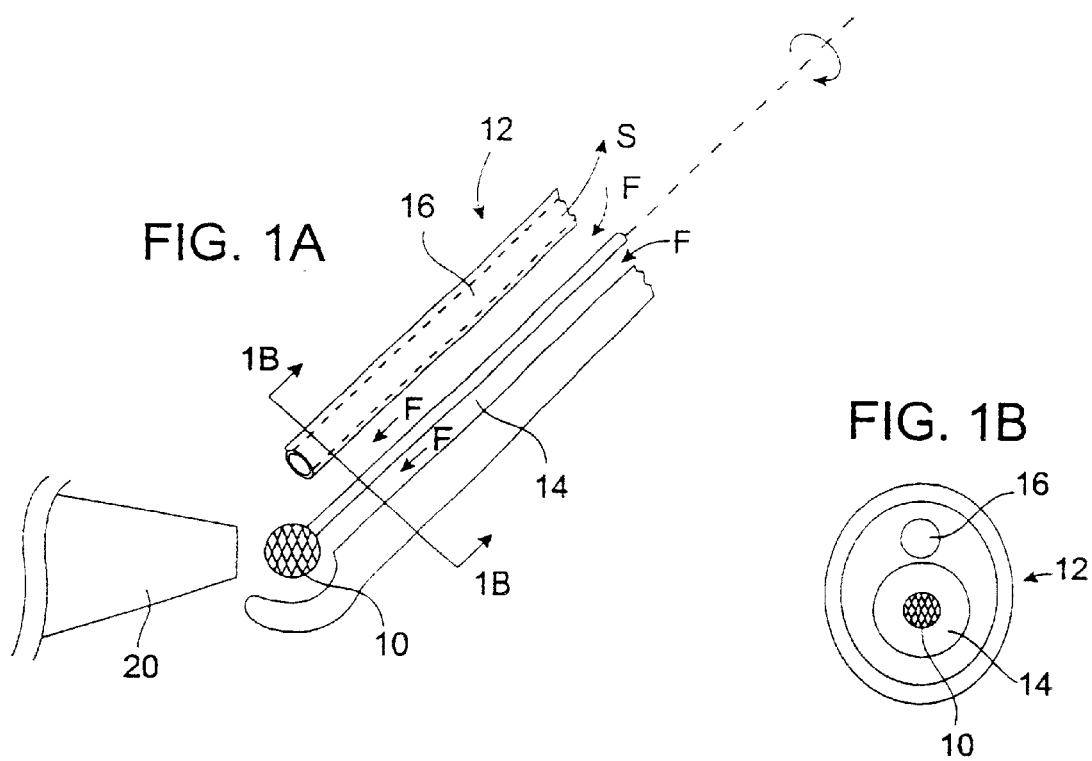
FIG. 1A
FIG. 1B
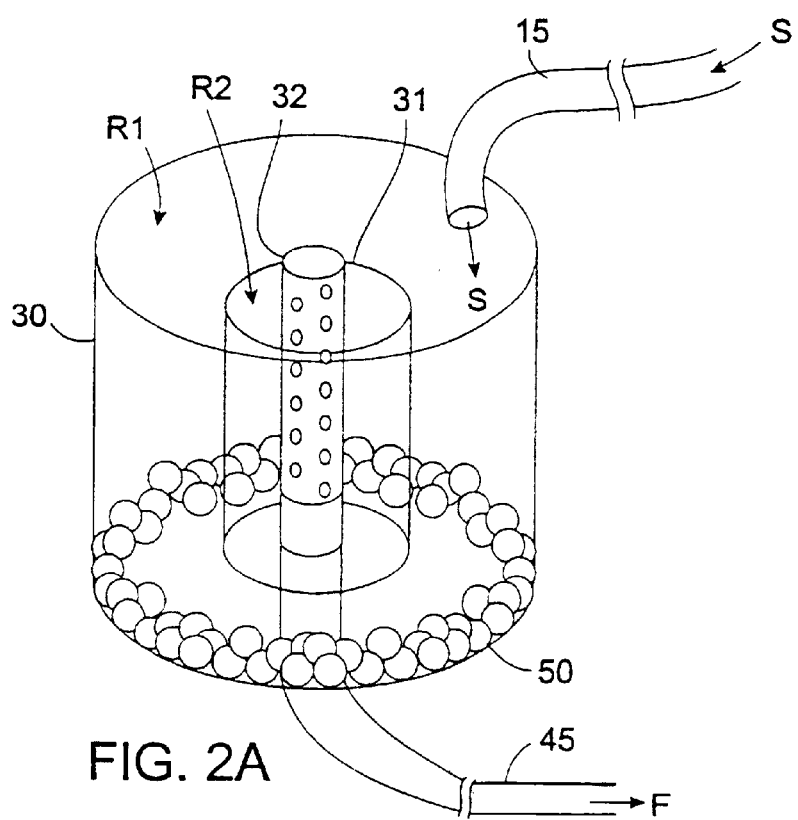
FIG. 2A

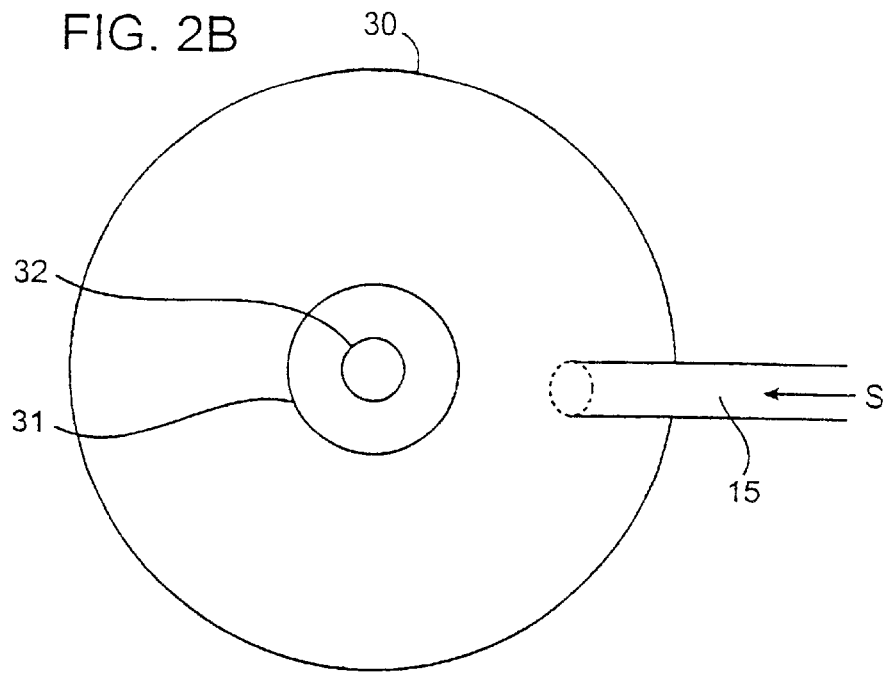
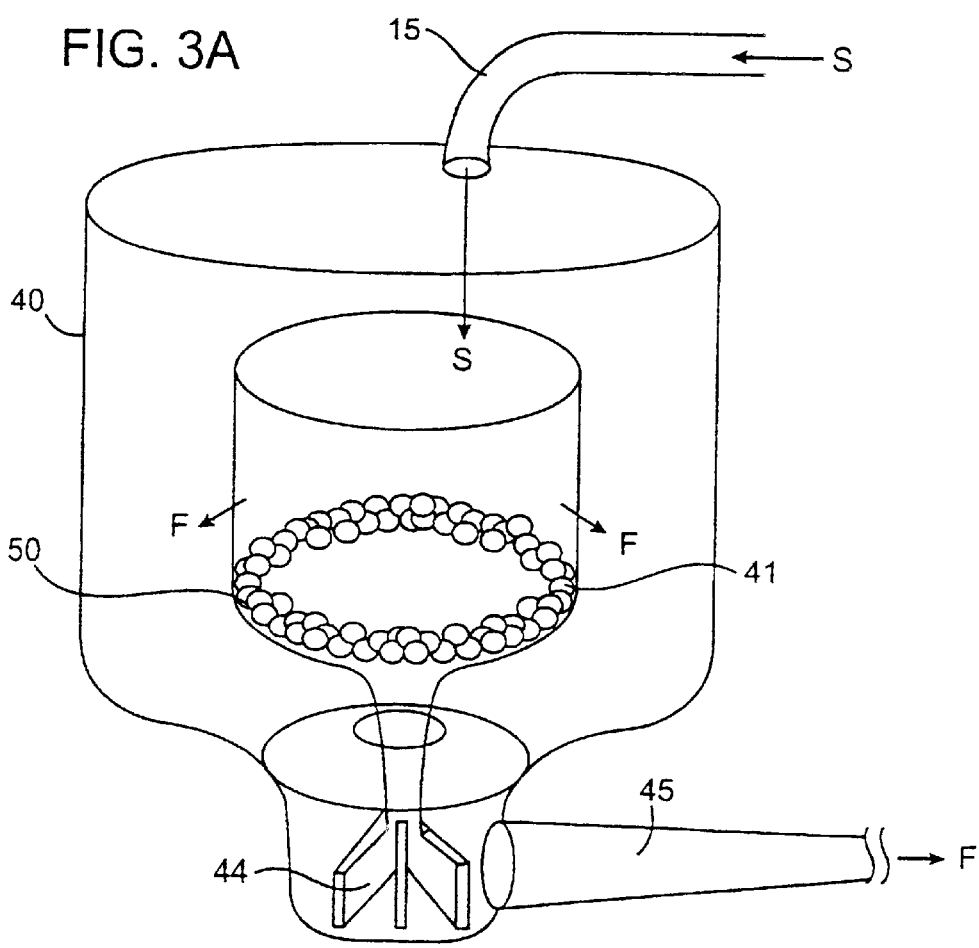

BONE SLURRY RECOVERY

CROSS-REFERENCES TO RELATED APPLICATIONS

This application claims the benefit of prior provisional application No. 60/154,449, filed on Sep. 17, 1999, the full disclosure of which is incorporated herein by reference.

BACKGROUND OF THE INVENTION

When accessing a patient's spinal region or intervertebral spaces during various surgical procedures, such as when performing a diskectomy, it is typically necessary to remove portions of various spinal bones to provide access to the operative site. Traditionally, the portions of the various spinal bones which are removed when accessing the patient's spinal region or intervertebral space are simply flushed away from the operative site and discarded.

This represents a waste of material as bone tissue can be used in various medical procedures. For example, when inserting intervertebral implants in a patient's intervertebral space, it is often desirable to insert bone allograft material into passages in the implant since such bone allograft material typically promotes bone ingrowth through the implant, resulting in bone fusion.

SUMMARY OF THE INVENTION

The present invention provides systems for recovering particles of bone which have been cut or ground away from an operative site by an abrading or cutting instrument and have been flushed from the operative site in a fluid slurry suspension. An advantage of the present invention is that it facilitates recovery of bone particles such that these recovered particles can then be used in other surgical procedures, for example, being compacted into the passageways in an intervertebral implant, to promote intervertebral bone growth.

Operating as a self-contained system, the present invention can be used to provide a rapid recovery of bone particles in real time, such that the bone particles removed and recovered by the present invention can be implanted back into the same patient during the surgical procedure (preferably after cleaning, as required). By recovering bone material and then implanting that same recovered bone material into the same patient, the need to rely on bone allograft transplants from other patients is reduced, thereby avoiding tissue rejection problems.

In one preferred aspect, the present invention provides systems for recovering bone material by passing a fluid slurry of bone particles through a filter (which may optionally spin centrifugally) or over a spill-separation partition which separates two different reservoirs.

In additional aspects, the present invention further comprises a device or devices for removing the bone slurry from the patient, wherein such device or devices may optionally comprise irrigation and fluid suctioning systems as well as systems for grinding, cutting, shaving or abrading bone tissue so as to yield small particles of bone tissue material, (which are then removed from the patient in a slurry, and are later recovered in accordance with the present invention). In one preferred aspect, a single multi-purpose device may optionally by used to provide the irrigation, suction and the grinding, cutting, shaving, or abrading necessary to yield the bone particles which are then carried into the spill-separation or filtering recovery portion of the system.

In various aspects of the invention, the present system can be operated in an "open" manner in which external irrigation fluid is supplied to the system, and waste fluid is expelled by the system. Alternatively, the present system can also be operated in a "closed" manner in which fluid is re-circulated such that the irrigation fluid is supplied from the outlet of the bone particle separation/filtration portion of the system (i.e.: after the bone articles have been removed from the slurry, the resulting substantially purified liquid is then used for irrigation, picking up more bone particles at the operative site, and delivering these particles in a slurry into the bone particle recovery portion of the system.

BRIEF DESCRIPTION OF THE DRAWINGS

FIG. 1A is a sectional perspective view of a cutting or abrading instrument having an internal irrigation lumen and a suction lumen, with an abrasive rotating burr disposed within irrigation lumen.

FIG. 1B is a cross sectional view taken along line 1B—1B in FIG. 1.

FIG. 2A is a perspective view of a dual reservoir spill-separation system for removing bone particles suspended in a fluid slurry.

FIG. 2B is a top plan view of the system of FIG. 2A.

FIG. 3A is a perspective view of a centrifugal system for removing bone particles suspended in a fluid slurry.

DESCRIPTION OF THE SPECIFIC EMBODIMENTS

The present invention comprises a variety of systems which are adapted to recover small particles of bone tissue which are removed in a fluid suspension (i.e.: a slurry) from an operative site in the patient. In various aspects, the present invention comprises novel gravity-based spill-separation, filtering and centrifugal separation systems for removing particulate matter from a slurry.

In additional aspects, the present invention further comprises a device or devices for removing the bone slurry from the patient, and optionally may comprise irrigation and fluid suctioning systems as well as systems for grinding, cutting, shaving or abrading bone tissue so as to yield small particulate amounts of bone tissue material, (which are then removed from the patent in a slurry, and later recovered by the present invention).

In various aspects of the invention, the present system can be operated in an "open" manner in which external irrigation fluid is supplied to the system, and waste fluid is expelled by the system. Alternatively, the present system can also be operated in a "closed" manner in which fluid is re-circulated such that irrigation fluid is supplied from the outlet of the bone particle separation/filtration portion of the system.

Figure 8:
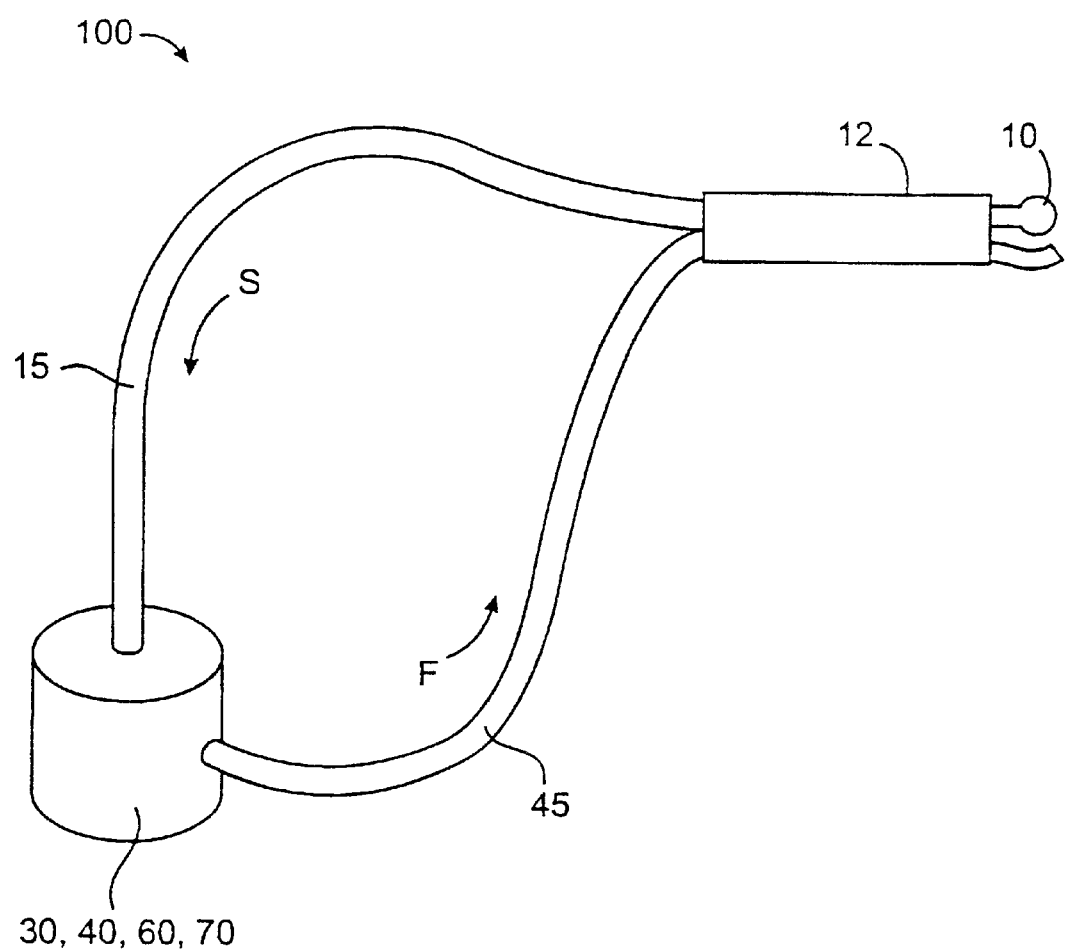
FIG. 8 is a schematic of a "closed" system on accordance with the present invention.
Figure 9:
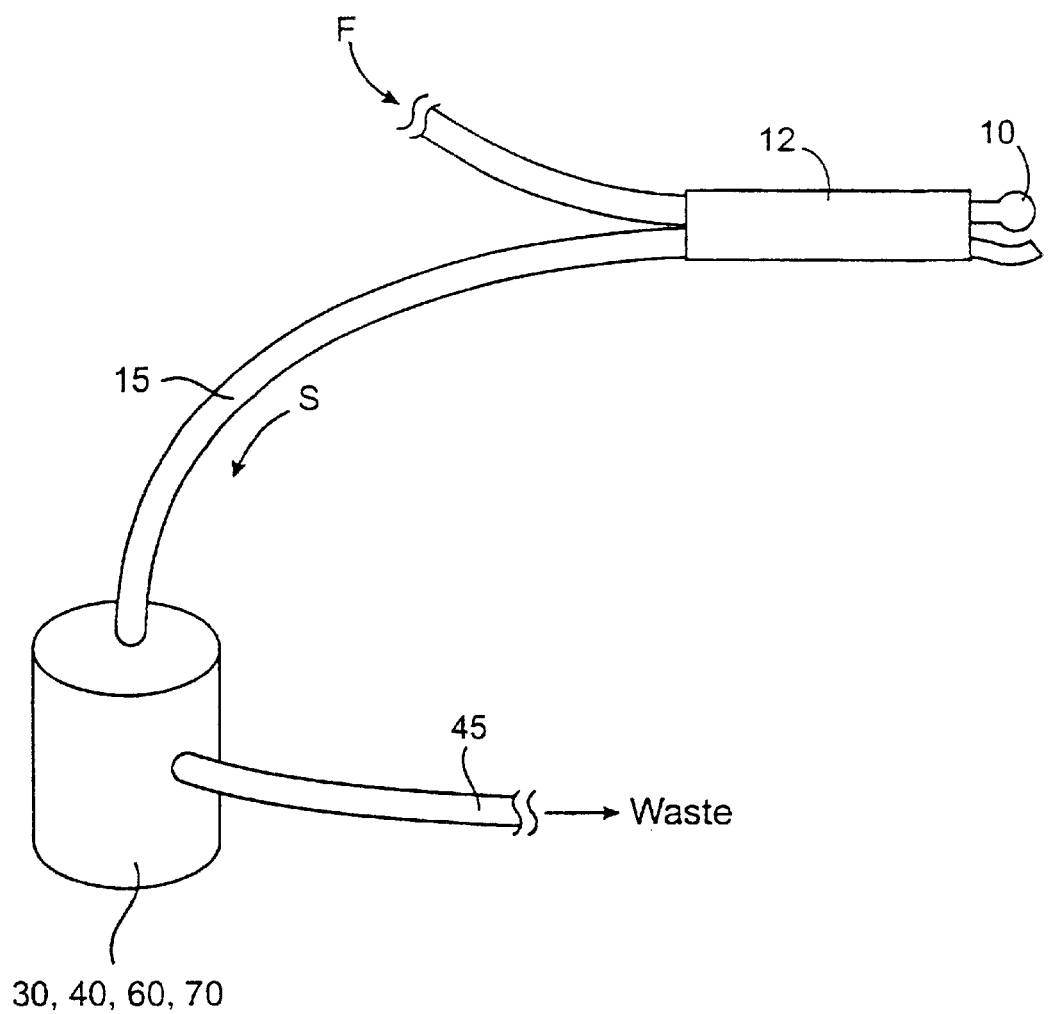
FIG. 9 is a schematic of an "open" system in accordance with the present invention.

Accordingly, various novel devices of the present invention are illustrated first, followed by illustrations of novel systems which incorporate these various novel devices. Specifically, FIGS. 1A and 1B illustrate a device for providing simultaneous irrigation, suction and tissue grinding; FIGS. 2A to 7 illustrate various devices for recovering bone particles from a fluid slurry; and FIGS. 8 and 9 illustrate respective closed and open systems incorporating the respective devices of FIGS. 1A to 1B and 2A to 7.

Referring first to FIGS. 1A and 1B, a rotating burr 10 is shown disposed within an irrigation lumen 14 of an instrument 12. As illustrated, instrument 12 comprises a grinding or abrading instrument, but any suitable tissue cutting, boring, scraping, shaving or gauging instruments which are adapted to yield small particles of bone tissue are contemplated for use as instrument 12 in the system of the present invention.

As illustrated, instrument 12 comprises a rotating burr 10 which may be advanced to a position such that it contacts and rubs or grinds against bone 20. Bone 20 may preferably comprise a cortical-cancellous bone and abrading/cutting instrument 12 may preferably be introduced into the patient either in a cannulated minimally invasive surgical approach, or alternatively by way of an open surgical approach.

Irrigation channel 14 surrounds burr 10 as shown, and a suitable irrigation fluid F is pumped distally through irrigation channel 14 passing over burr 10, maintaining a fluidic level around burr 10, as shown. As burr 10 rotates, its abrasive surfaces will wear away at the lamina of bone 20, producing very small particles of bone 20. A suction lumen 16 is disposed within abrading/cutting instrument 12, such that a slurry S of bone particles suspended in fluid F can be pumped distally out of instrument 12, passing through tube 15 (as seen in FIGS. 2A to 3B, 8 and 9) to a bone particulate recovery system, including, but not limited to, any of the systems of FIGS. 2A to 7.

It is to be understood that rotating burr 10 need not be disposed within irrigation channel 14. Different designs are possible, including designs in which the irrigation channel is separate from the cutting/abrading/grinding portion of the device. It is also to be understood that designs in which separate devices for providing irrigation, fluid suction and removal, and bone particle generation (e.g.: through scraping or grinding away bone tissue) are also included within the scope of the present invention.

In accordance with various aspects of the present invention, slurry S comprises bone particles having an average size of 2 to 5 microns, although various bone particles may be larger depending upon how these particles initially break away from the bony structure at the operative site.

Figure 2C:
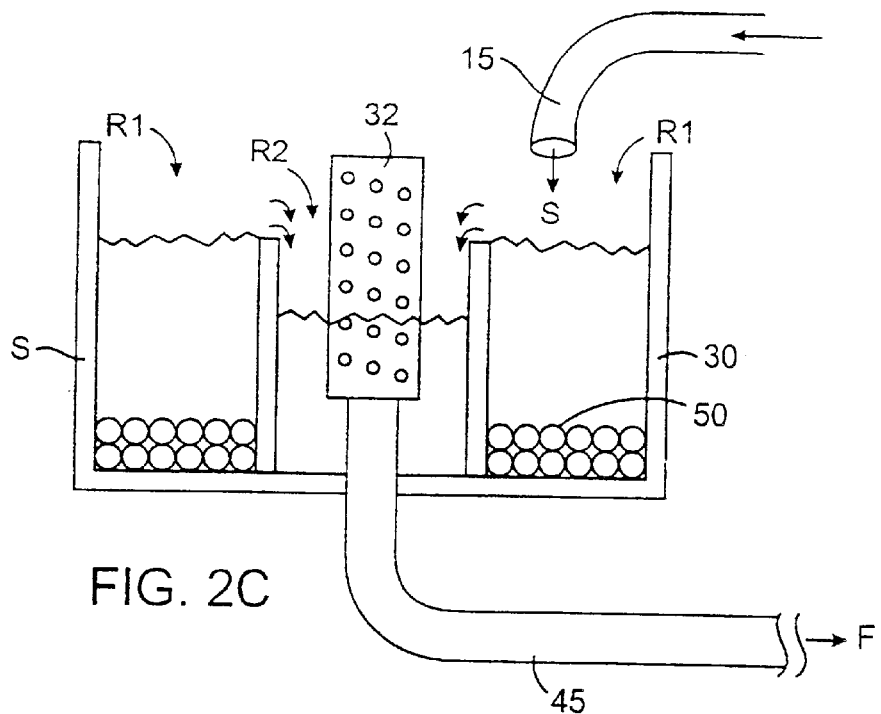
FIG. 2C is a cross-sectional view of the system of FIG. 2A.

FIGS. 2A and 2B illustrate a dual reservoir gravity based spill-separation system for recovering bone particulate matter. This aspect of the invention comprises a recovery canister 30, and an internal barrier 31 which surrounds a cylindrical filter 32. A first reservoir R1 is formed between the wall of recover canister 30 and internal barrier 31, and a second reservoir R2 within internal barrier 31. As seen in FIG. 2C, the height of internal barrier 31 is less than the height of the walls of recovery canister 30. Accordingly, the fluid slurry collected in reservoir R1 of recovery canister 30 will tend to spill over the top of internal barrier 31 into reservoir R2, with bone particles 50 settling to the bottom of reservoir R1 for collection, since the upper portions of the fluid slurry, (which contain the smallest amount of bone particles therein), are siphoned off at the top of their fluid level, spilling over into reservoir R2 between internal barrier 31 and filter 32. Optional filter 32 is preferably dimensioned to further ensure that bone particles are removed from the fluid as the fluid passes therethrough for removal through outflow tube 34. A potential advantage of this system is that the bone particles may tend to sink to the bottom of reservoir R1, such that filter 32 does not become clogged.

In various optional aspects of the invention, as illustrated in FIG. 8, fluid F passing out of canister 30 by way of tube 45 is re-directed into irrigation lumen 14, thus producing a "closed" system. Alternatively, in various optional aspects of the invention, as illustrated in FIG. 9, fluid F passing out of canister 30 by way of tube 45 is simply directed to waste, thus producing an "open" system.

Figure 3B:
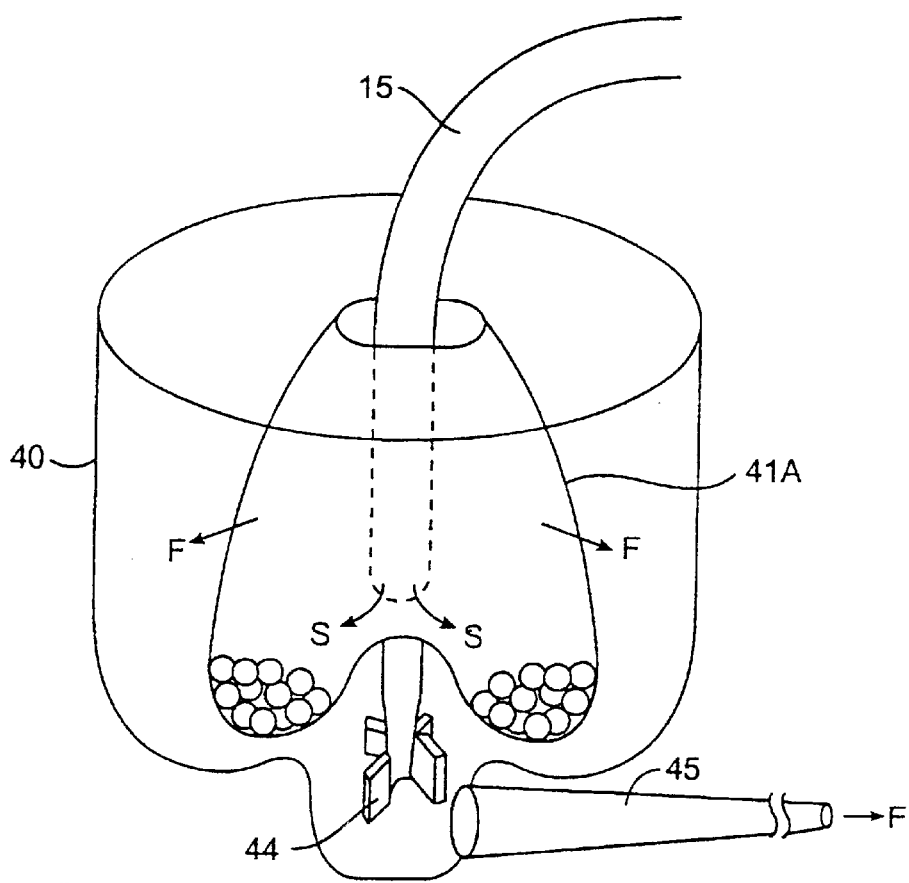
FIG. 3B is an alternate design of the system of FIG. 3A, with the inner rotating portion instead having a curved bottom and slanting sides which are adapted to trap bone particles therein.

In an alternate aspect of the invention, as shown in FIG. 3A, bone particulate recovery is accomplished by a cylindrical filter 41 positioned within recovery canister 40. As filter 41 is rotated, it acts as a centrifuge. Accordingly, bone particles 50 will thus tend to concentrate against the interior wall of filter 41 (as well as at the bottom of filter 41 due to gravity). Various advantages to this system include: (1) the bone particles 50 recovered are moist instead of wet due to the spinning action of filter 41, (2) bone particles 50 are compacted due to the centrifugal spinning, and are thus east to remove, and (3) bone particles 50 are likely to be evenly distributed around the interior wall of filter 41, thus preventing filter 41 from clogging. FIG. 3B shows an alternate design of the filter system of FIG. 3A, with filter 41A having a curved bottom and slanting sides, which are adapted to trap bone particles 50 therein as shown. As can also be seen, tube 15 may be extended deeply into the center of rotating filter 41A.

As can be seen in both the bone particulate recovery systems of FIGS. 3A and 3B, the slurry S of fluid and bone particles is preferably deposited into the center of filter 41 with the centrifugal rotation of filter 41 causing bone particles 50 to be forced against the sides of filter 41 while purified fluid F passes therethrough such fluid F can be withdrawn from canister 40, such as by way of tubing 45. As such, a substantially purified fluid F can be withdrawn through tube 45, while insuring that bone particles 50 do not pass through filter 41, but are instead retained for further recovery within filter 41. In an optional preferred aspect, tubing 45 which is used to withdraw fluid F from canister 40 can also be used to as a hydraulic turbine which turns propeller 44, thereby causing filter 41 to rotate.

Alternate filtering systems for bone particulate recovery are provided in FIGS. 4 and 5, in which slurry S is passed through a fine non-rotating filter which traps the bone particulate matter for recovery, as follows.

Figure 4:
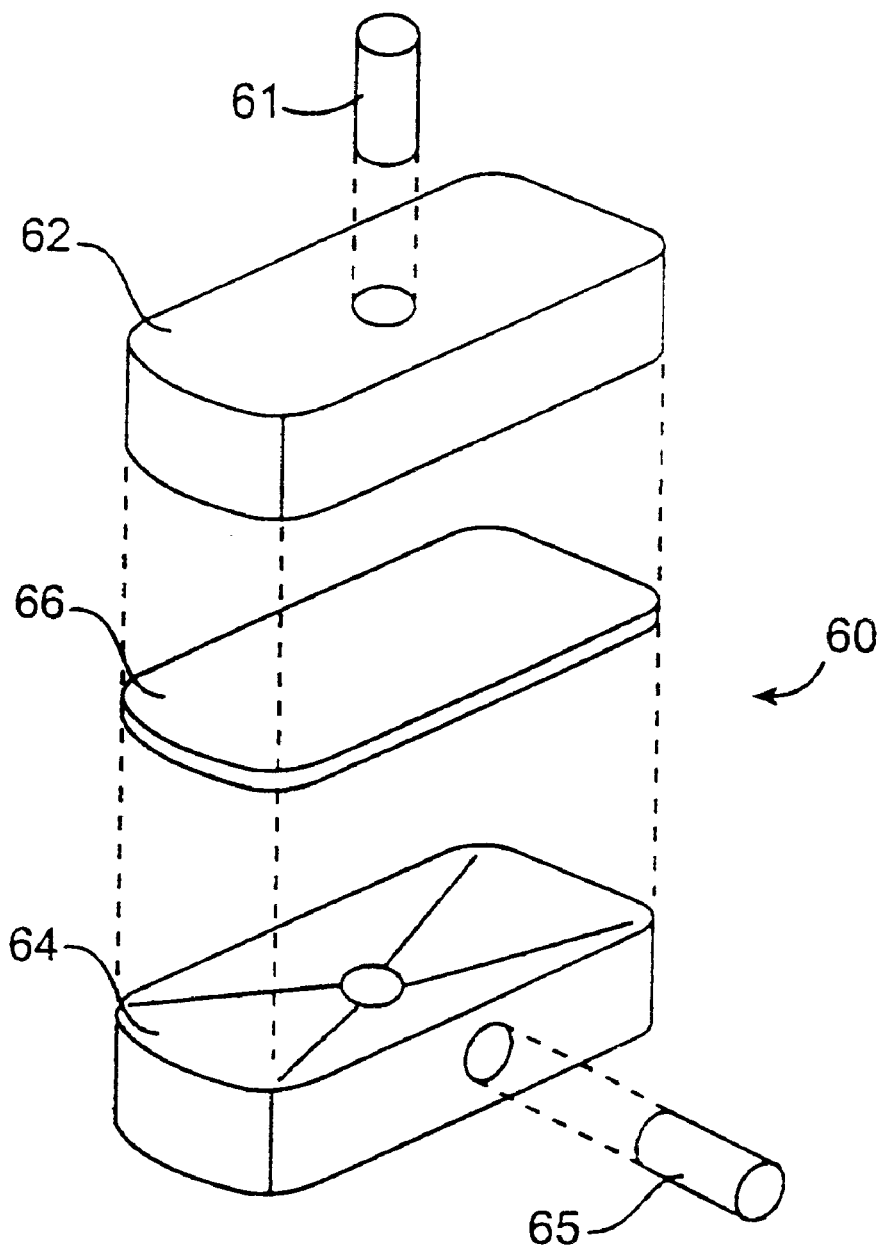
FIG. 4 is an exploded perspective view of a filtering system for removing bone particles suspended in a fluid slurry.

Referring to FIG. 4, a bone particulate recovery system 60 is provided. System 60 comprises a lid 62 and a bottom 64 with a filter 66 positioned therebetween. Together, slurry S enters system 60 through connector 61, passing through filter 66, and exits through connector 65. Connectors 61 and 65 may comprise barbed PVC connectors, such that inflow and outflow tubing (15 and 45) can easily be connected thereto.

Figure 5:
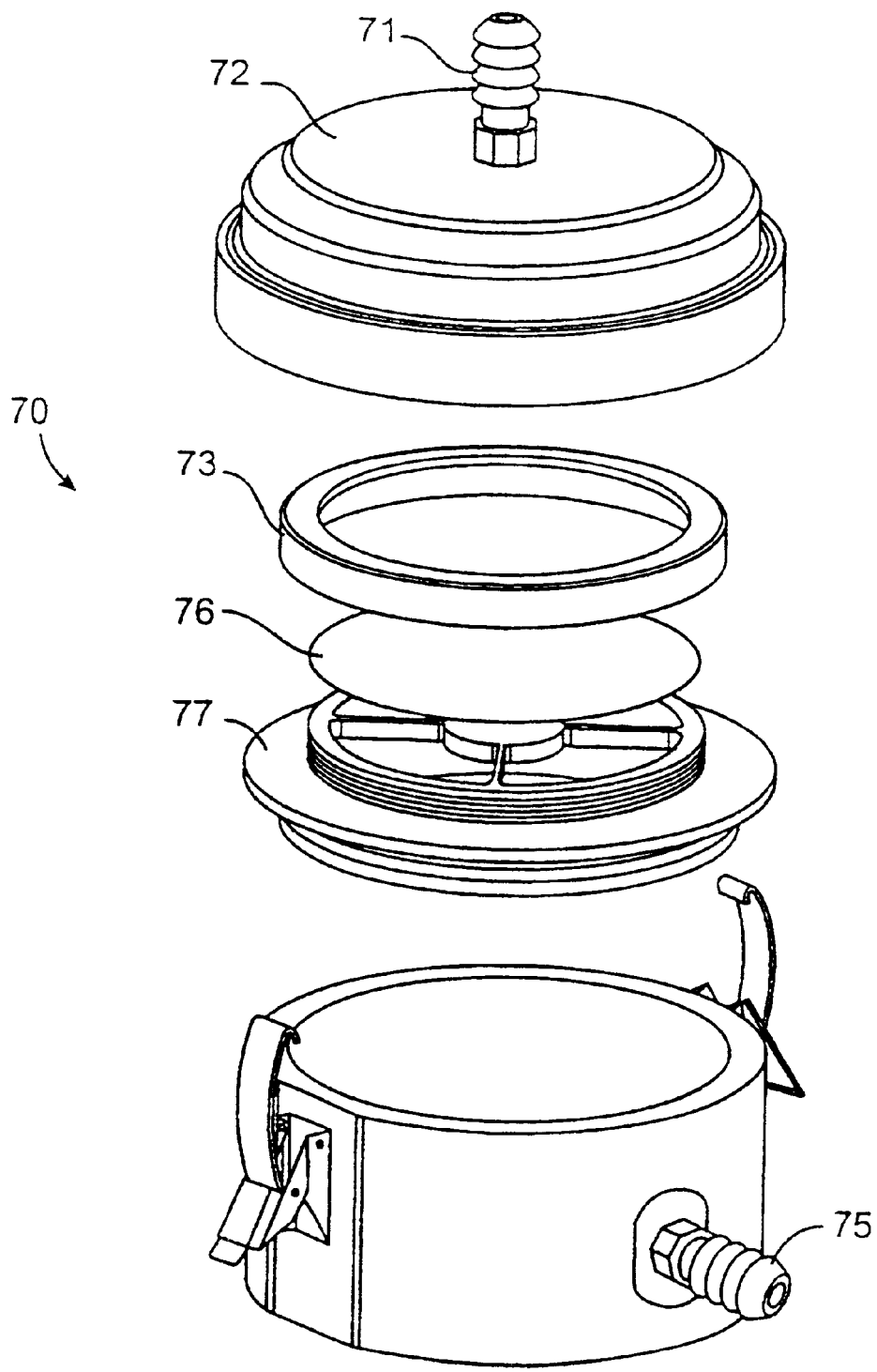
FIG. 5 is an exploded perspective view of another filtering system for removing bone particles suspended in a fluid slurry.
Figure 6:
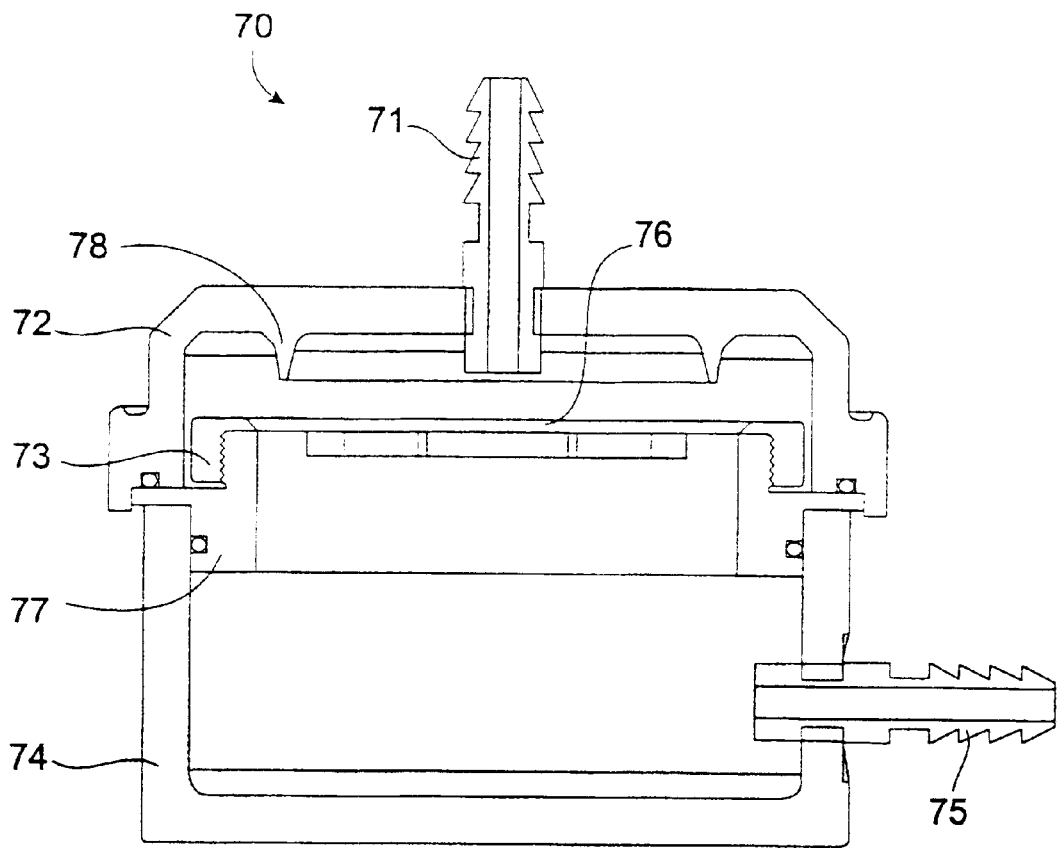
FIG. 6 is an assembled sectional elevation view of the filtering system of FIG. 5.
Figure 7:
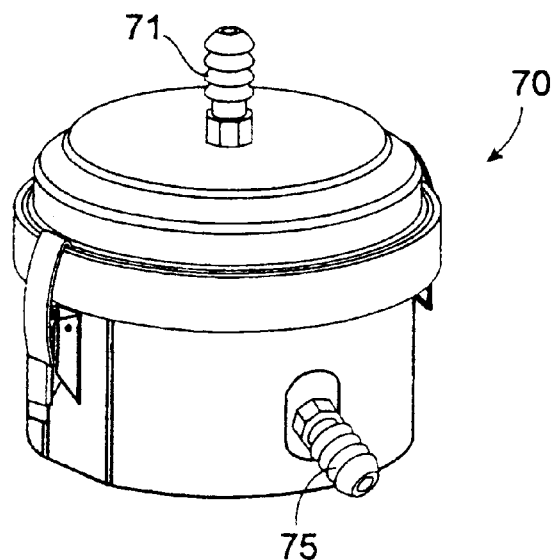
FIG. 7 is an assembled perspective view of the system of FIG. 5.

Referring to FIGS. 5 to 7, an alternate bone particulate recovery system 70 is provided. System 70 comprises a lid 72, a base 74 and a filter media 76 supported therebetween.

A filter retaining nut 73 is used to securely fasten filter 76 to the top of filter tray 77. A fluid slurry inflow connector 71, and outflow connector 75 are provided for convenient attachment of flow tubing thereto. In an alternate aspect, inflow connector can be attached to a side of system 70 (rather than to lid 72) such that lid 72 can be removed, permitting easy removal of the bone particulate matter, without spilling the fluid contents of the system. A ring-shaped flange 78 in lid 72 helps direct inflow slurry of fluid and bone particles to filter media 76. Opening lid 72 provides easy access to collected material. Moreover, simple opening of lid 72 makes it easy to change filter media (e.g. to different pore size filters) if desired. Additional various advantages of this system include the ability to interoperatively remove the bone particles from the filter media without replacing the media. In addition, the system is free-standing, reusable and potentially autoclavable.

As shown in FIG. 8, the present invention may be operated as a self-contained "closed" system in which slurry S passes through tube 15 from instrument 12 to system 30, 40, 60 or 70 for recovery of the bone particulate matter. Thereafter, the outflow of system 30, 40, 60 or 70 may be returned to instrument 12 (passing through irrigation lumen 14) as irrigation flow F.

Alternatively, as shown in FIG. 9, the present invention may be operated as an "open" system in which slurry S passes through tube 15 from instrument 12 to system 30, 40, 60 or 70 for recovery of the bone particulate matter. Thereafter, the outflow of system 30, 40, 60 or 70 is directed to waste. In this aspect of the invention, a fluid irrigation system (not shown) may be used to provide a steady stream of irrigation fluid to the surgical site.

In either of the systems of FIGS. 8 or 9, fluid pumps can be added to ensure a steady flow of irrigation fluid F onto the operative site and a steady fluid suction of slurry S away from the operative site.

What is claimed is:

1. A system for recovering bone particles from a fluid removed from a patient, comprising:
    a cutting instrument yielding the fluid;
    a housing having first and second fluid reservoirs therein;
    a flow inlet in fluid communication with the instrument and entering the first fluid reservoir;
    a flow outlet in fluid communication with the instrument and exiting the second fluid reservoir;
    a partition having a top and separating the first and second fluid reservoirs, wherein the partition is configured to allow the fluid to spill over the top from the first fluid reservoir to the second fluid reservoir; and
    a filter positioned between the second fluid reservoir and the flow outlet.

2. A system for recovering bone particles removed from a patient, comprising:
    an instrument for yielding bone particles;
    a housing having first and second fluid reservoirs therein;
    a flow inlet in fluid communication with the instrument and entering the first fluid reservoir;
    a flow outlet in fluid communication with the instrument and exiting the second fluid reservoir;
    a partition having a top and separating the first and second fluid reservoirs; and
    a fluid containing bone particles filling the first reservoir wherein the partition is configured to allow the fluid to spill over the top of the partition and into the second reservoir.

3. The system of claim 2, wherein the fluid in the first reservoir has a higher concentration of bone particles than the fluid in the second reservoir.

4. A method of recovering bone particles from a fluid slurry, comprising:
    filling a first fluid reservoir with the slurry such that fluid passes over a top of a partition and into a second fluid reservoir, whereby the bone particles collect in the first fluid reservoir such that the fluid which passes over the top of the partition and into the second fluid reservoir has a substantially reduced concentration of bone particles therein; and
    recovering the bone particles from the first fluid reservoir; and
    directing the fluid from the second fluid reservoir to irrigate an operative site.

5. A system for recovering bone particles removed from a patient, comprising:
    a housing;
    a rotatable filter mounted within the housing, separating a first fluid reservoir disposed within an inner perimeter of the filter from a second fluid reservoir disposed around an outer perimeter of the filter;
    a flow inlet entering the first fluid reservoir; and
    a flow outlet exiting the second fluid reservoir, wherein rotation of the filter generates a centrifugal force which separates the bone particles from fluid passing through the filter from the first reservoir to the second reservoir, wherein the rotatable filter has outwardly slanted sides and a curved bottom.

6. A system for recovering bone particles removed from a patient, comprising:
    a sub-system for removing particles of bone at an operative site on a bony structure;
    a sub-system for irrigating the operative site to yield a slurry comprising the bone particles;
    a sub-system for removing the slurry from the operative site;
    a sub-system for recovering the bone particles from the slurry, wherein the sub-system for removing the slurry from the operative site is in fluid communication with the a sub-system for recovering the bone particles from the slurry, such that the slurry is directed into the sub-system for recovering the bone particles from the slurry, wherein fluid outflow from the sub-system for recovering the bone particles from the slurry is directed to the sub-system for irrigating the operative site.

7. A method of recovering bone particles removed from a patient, comprising:
    generating particles of bone at an operative site on a bony structure;
    irrigating the operative site to yield a slurry comprising the bone particles;
    suctioning the slurry away from the operative site; and
    directing the slurry into a system for separating the bone particles from the slurry; and
    directing fluid outflow of the system for separating the bone particles from the slurry to irrigate the operative site.

* * * * *